United States Patent [19]

Wright et al.

[11] Patent Number: 4,722,338

[45] Date of Patent: Feb. 2, 1988

[54] MEDICAL INSTRUMENT FOR REMOVING BONE

[75] Inventors: Dale W. Wright, Saginaw; David W. Wright, Wixom, both of Mich.

[73] Assignee: Daniel Farley, Barrington, Ill.

[21] Appl. No.: 560,210

[22] Filed: Dec. 12, 1983

[51] Int. Cl.4 .............................................. A61B 17/32
[52] U.S. Cl. ................................................... 128/312
[58] Field of Search ............... 128/305, 310, 311, 312, 128/318, 325, 326, 346, 751, 752, 753, 754, 755

[56] References Cited

U.S. PATENT DOCUMENTS

| | | | |
|---|---|---|---|
| 571,040 | 11/1896 | DeVilbiss | 128/312 |
| 988,939 | 4/1911 | Hudson | 128/312 |
| 1,002,826 | 9/1911 | DeVilbiss | 128/312 |
| 1,040,523 | 10/1912 | DeVilbiss | 128/312 |
| 1,663,761 | 3/1928 | Johnson | 128/305 |
| 3,752,161 | 8/1973 | Bent | 128/312 |
| 4,201,213 | 5/1980 | Townsend | 128/312 |
| 4,316,468 | 2/1982 | Klieman et al. | 128/334 R |
| 4,574,803 | 3/1986 | Storz | 128/305 |

FOREIGN PATENT DOCUMENTS

| | | | |
|---|---|---|---|
| 0010321 | 4/1980 | European Pat. Off. | 128/755 |
| 230503 | 4/1911 | Fed. Rep. of Germany | 128/312 |

*Primary Examiner*—Robert Peshock
*Assistant Examiner*—Cary E. Stone
*Attorney, Agent, or Firm*—Allegretti, Newitt, Witcoff & McAndrews, Ltd.

[57] ABSTRACT

There is provided an improved forcep or rongeur having a jaw mechanism comprised of a barrel member having a honed cutting edge on one extremity thereof and having a shaft member located within and arranged for reciprocal motion. On the shaft member there is provided a plate member attached at one extremity to trap bone against the cutting edge. A lever mechanism is provided having paired handle levers joined by a pivot and having the barrel and shaft members attached to the handle levers between the handle portion and the pivot. On the shaft member there is further provided a cavity arranged to slide within the barrel progressively as the cutting operation proceeds, gradually drawing severed bone within the capturing cavity.

4 Claims, 6 Drawing Figures

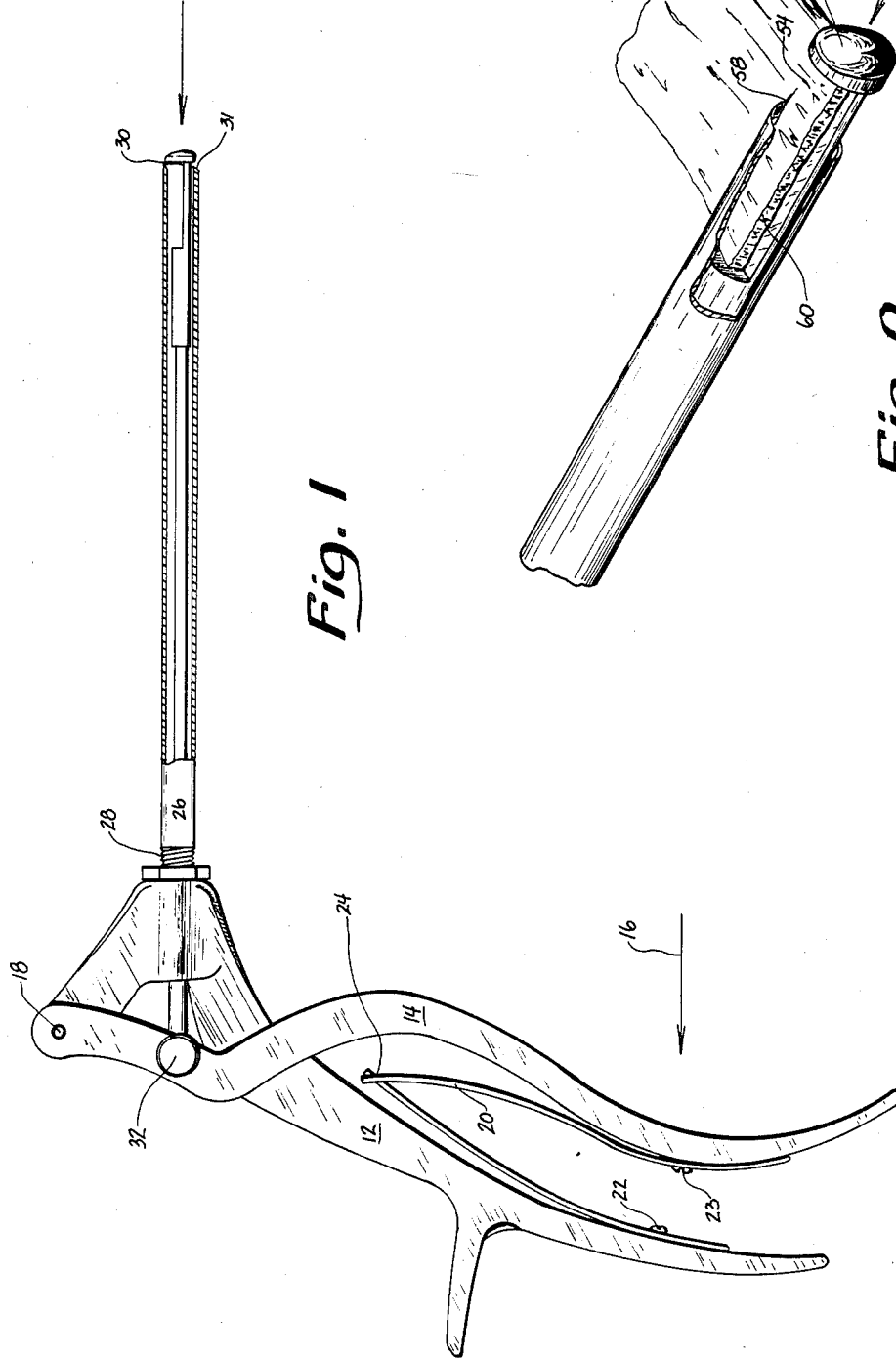

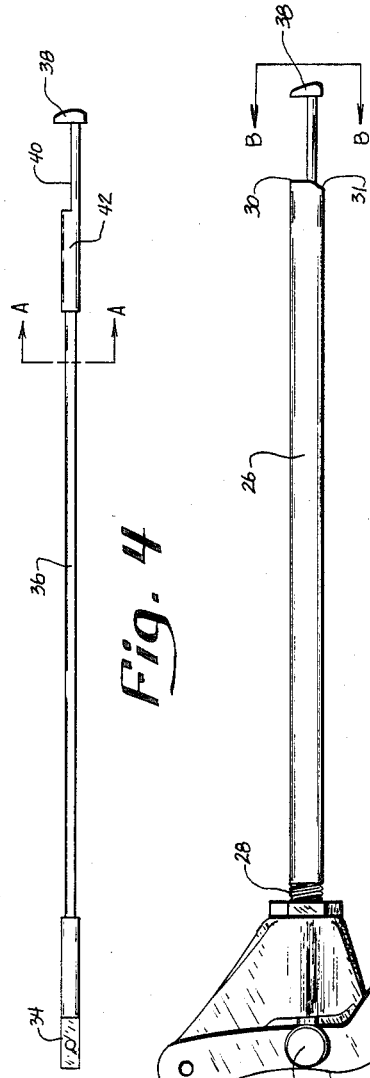
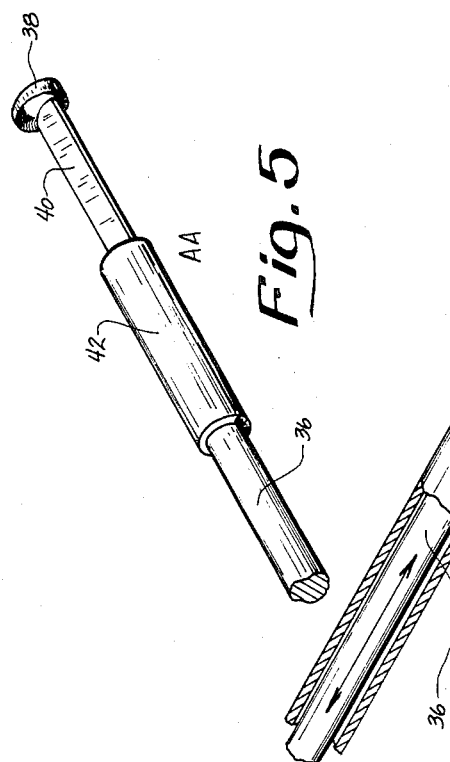
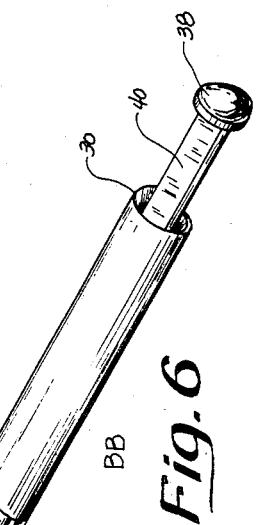
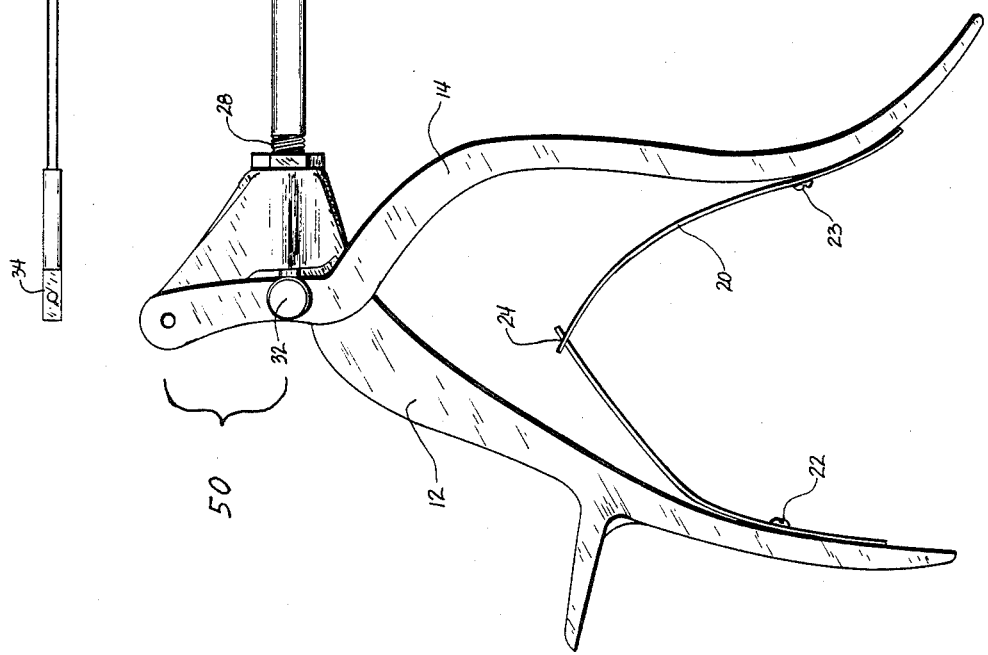

MEDICAL INSTRUMENT FOR REMOVING BONE

BACKGROUND OF THE INVENTION

This invention relates generally to forceps of the rongeur or bone cutting type. It has long been an object in the art to provide simple, inexpensive forceps capable of easy disassembly and cleaning, and most importantly capable of safe and efficient operation. Prior patents issued in this art have proposed possible solutions. Typical of the prior art is the patent issued to De Vilbiss, U.S. Pat. No. 1,040,523, which provides a lever mechanism comprising a handle having two sides arranged to pivot towards one another about a central axis. On extensions of these handle members there is provided a jaw mechanism comprising a first movable jaw arranged to travel within a slot defined within a second movable jaw. Bone seized between the jaws is pulled within the slot as it is cut. A problem associated with this and other mechanisms in the art is that uncontrolled force is applied to the bone surface surrounding the cutting area, such that possible bone breakage and splintering may occur. If operating near the spinal cord, possible nerve damage may result. Further, bone chips cut from the bone structure are not well contained by the instrument and contamination of the wound may result. Finally, with the pivot placed between the jaw mechanism and the lever handles limited mechanical advantage is available, making the instrument tiring to use.

Accordingly, it is the primary aim of the present invention to provide an approved forcep or rongeur for cutting bone wherein the bone chips, once severed, are safely contained within the instrument and held therein until selectively ejected.

It is a further object of the present invention to provide a jaw-like mechanism wherein bone chips are immediately deposited within the capturing instrument as they are cut.

It is also an object of the present invention to eliminate uncontrolled forces in and about the cutting area to avoid possible bone breakage and splintering beyond the cutting area.

It is also an object of the present invention to modify the mechanical leverage to provide improved mechanical advantage for the device and to provide better control during operation.

Briefly stated there is provided an improved forcep or rongeur having a jaw mechanism comprised of a barrel member having a honed cutting edge on one extremity thereof and having a shaft member located within and arranged for reciprocal motion. On the shaft member there is provided a plate member attached at one extremity to trap bone against the cutting edge. A lever mechanism is provided having paired handle levers joined by a pivot and having the barrel and shaft members attached to the handle levers between the handle portion and the pivot. On the shaft member there is further provided a cavity arranged to slide within the barrel progressively as the cutting operation proceeds, gradually drawing severed bone within the capturing cavity, allowing for a cutting action rather than a crushing action, thereby relieving pressure on the plate member and thus reducing the possibility of breaking said member while cutting bone structures.

Other objects and advantages of the invention will become apparent upon reading the following detailed description and upon reference to the drawings, in which:

FIG. 1 is a perspective view partially cut away of the preferred embodiment of the present invention.

FIG. 2 is an enlarged perspective view of the distal end of the instrument in operation.

FIG. 3 is a side view of the preferred embodiment of the present invention.

FIG. 4 is a side view of the shaft member of the present invention.

FIG. 5 is a perspective view of the end of the shaft of FIG. 4 viewed along the line AA.

FIG. 6 is a perspective view partially cut away of the device of FIG. 3 viewed along the line BB.

While the invention will be described in connection with the preferred embodiment, it will be understood that we do not intend to limit the invention to that embodiment. On the contrary, we intend to cover all alternatives, modifications and equivalents as may be included within the spirit and scope of the invention as defined by the appended claims.

DESCRIPTION OF THE PREFERRED EMBODIMENT

Turning first to FIG. 1 there is shown the forceps of the preferred embodiment of the present invention. Specifically there is shown a paired handle member 12 and 14 arranged to be held within the human hand and pulled together in the direction of the arrow 16 much in the same manner as a pair of pliers. This handle pair is arranged to pivot about the axis 18 and each is arranged as shown in the drawing to support and actuate the barrel and shaft cutting mechanism as more fully described below.

A squeezing force on the paired handle members closes the handles in the direction of the arrow 16, and concurrently compresses the intermediate spring 20 located between the handle pair. This generates a returning force to return the handles to their starting position as shown in FIG. 3. The return spring is typically of spring steel made of distinct and separate members, each rigidly attached to respective individual handle members at the lower extremity 22 and 23 respectively, while being hingedly interlocked at the intermediate contacting point 24.

Rigidly attached by screw thread means to the first member of the handle pair there is provided a barrel member 26 comprised of a cylindrical tube having external threads 28 at its point of attachment to the handle, and having at its other extremity a honed edge 30 (more clearly shown in FIG. 6) for cutting bone pressed thereagainst. Generally, only the upper edge is honed for cutting with the lower edge 31 being angled away from the end to avoid contact with the reciprocating mechanisms.

Mounted for reciprocal motion within said barrel there is provided a shaft member pivotally attached at axis 32 to said second handle member and arranged to selectively protrude from said barrel at its other extremity. This shaft member (FIG. 4) is comprised of a first attachment portion 34 for connection to the pivot mount at the handle, and a force transmission portion 36 for transmitting the force of the handle leverage mechanism remotely to the site of the bone cutting at the distal end of the barrel. Finally, there is a bone cutting and trapping portion comprised of a contoured plate 38 mounted transversely to the distal end of the shaft. This plate is shown with increased thickness in the vicinity of its attachment to the shaft to resist breakage. Within said shaft there is provided a cavity portion 40 (see FIG. 5) defined by a depression on such shaft. In the preferred embodiment this cavity is formed by a flat depression represented by a cut away portion of said shaft. Finally, a sealing portion 42 is provided to close the gap between the barrel and the shaft as the shaft end is drawn into the barrel. This sealing portion acts to maintain the barrel free of debris and serves to eject bone fragment following a cutting sequence.

To improve the mechanical advantage of the forceps, increased leverage is provided by attaching the barrel and shaft between the handle pivot and the handle grasping portion where hand pressure is applied during the squeeze. By varying the distance 50 between the barrel and shaft attachment points and the pivot, mechanical advantage can be set to provide comfortable operation during strenuous bone cutting procedures. Additionally, the tendency of the forceps to move during actuation is reduced as the spacing 50 is increased while fine control is retained by keeping the grasped portion of the handle near the barrel and shaft attachment.

In operation (see FIG. 2) there is shown a bone segment 52 with an unsevered portion 54 trapped between the shaft and plate 56 and the honed edge of the barrel 58. As the shaft is drawn towards the barrel, severed bone 60 is captured within the barrel. Once the stroke has been completed the forceps are removed from the cutting site, inverted, and the shaft extended from the barrel to facilitate deposit of the severed bone into the proper receptacle.

There has been shown and described an improved forcep or rongeur having a jaw mechanism comprised of a barrel member having a honed cutting edge on one extremity thereof and having a shaft member located within and arranged for reciprocal motion. On the shaft member there is provided a plate member attached at one extremity to trap bone against the cutting edge. A lever mechanism is provided having paired handle levers joined by a pivot and having the barrel and shaft members attached to the handle levers between the handle portion and the pivot. On the shaft member there is further provided a cavity arranged to slide within the barrel progressively as the cutting operation proceeds, gradually drawing severed bone within the capturing cavity.

We claim:

1. A medical instrument for cutting and removing bone comprising:
    a rigid barrel member having a cutting edge defined at one extremity thereof;
    a shaft member positioned coaxially within said barrel member and arranged for reciprocal motion therein, said shaft member having a plate member mounted at one extremity thereof transverse to said shaft member and a defined cavity proximate to said plate member; and
    lever means for reciprocally translating said shaft member within said barrel (a) to cause said plate to reciprocate with respect to said barrel trapping said bone between said cutting edge and said plate and (b) to cause said cavity to reciprocate with respect to said barrel capturing bone severed by said cutting edge within said cavity; said reciprocal translation of said shaft member within said barrel defining an open position and a closed position of said medical instrument; said closed position being defined by said plate transversely abutting said cutting edge and said open position being defined by said plate being spaced from said cutting edge such that as said medical instrument is moved from said open position to said closed position, said plate is brought into abutting contact with said cutting edge; said barrel remaining stationary while said medical instrument is moved between said open position and said closed position.

2. The medical instrument of claim 1 wherein said shaft member has further defined thereon a sealing portion having a diameter sufficient to provide an effective sealing fit within said barrel for facilitating the capture of severed bone within said barrel and the selective ejectment thereof.

3. The medical instrument of claim 2 wherein said cutting edge is comprised of a honed edge of said barrel.

4. The medical instrument of claims 1, 2 or 3 wherein said lever means is comprised of a pivoted handle mechanism having pivoted paired handle portions wherein said shaft and said barrel are connected to said handle mechanism at a point between said paired handle portions and said pivot.

* * * * *